United States Patent [19]

Lahoda et al.

[11] Patent Number: 4,695,441

[45] Date of Patent: Sep. 22, 1987

[54] MANUFACTURE OF SILANE

[75] Inventors: Edward J. Lahoda, Edgewood Borough; Herbert A. Burgman, Murrysville, both of Pa.; Young J. Kwon, Fruit Heights, Utah

[73] Assignee: Westinghouse Electric Corp., Pittsburgh, Pa.

[21] Appl. No.: 10,108

[22] Filed: Feb. 2, 1987

[51] Int. Cl.$^4$ ............................................. C01B 33/04
[52] U.S. Cl. .................................................. 423/347
[58] Field of Search ........................ 423/347; 556/471

[56] References Cited

U.S. PATENT DOCUMENTS 4,079,071  3/1978  Neale ................................... 423/347
4,506,087  3/1985  Fischer et al. ....................... 556/471

*Primary Examiner*—John Doll
*Assistant Examiner*—Lori S. Freeman
*Attorney, Agent, or Firm*—R. D. Fuerle

[57] ABSTRACT

Disclosed is a method for making silane. A silicon tetrahalide having the general formula $SiX_4$ is reacted with a compound which can be alcohols to $C_4$, alkanes to $C_4$, alkenes to $C_4$ alkenes to $C_4$ or a mixture thereof, where X is independently selected from the halogens, to produce a product having the general formula $SiR_4$, where each R is independently selected from alkoxy to $C_4$, alkyl to $C_4$, alkylene to $C_4$ and alkenyl to $C_4$. The $SiR_4$ is then reacted with hydrogen to produce the silane.

15 Claims, No Drawings

MANUFACTURE OF SILANE

BACKGROUND OF THE INVENTION

The production of electronic grade silicon metal requires the use of a highly purified silicon-containing feed. One such feed is silane ($SiH_4$), which is typically made from metallurgical grade silicon. There are several methods of purifying this metallurgical grade silicon metal. However, these reactions must be carefully controlled so as to preclude the formation of free HCl, which would attack the reaction vessels and contaminate the silicon with corrosion products. In addition, high pressures and temperatures are required, followed by very low temperature distillation to separate the silane from the intermediate product, trichloro silane, and the contaminating HCl. Other disadvantages include use of a relatively high cost feed (metallurgical grade silicon) and very large internal recycle requirements which increase the operating cost associated with the process. Alternative processes have been proposed which are similar, but they tend to convert some of the high cost feed into low grade silicon tetrachloride. Methods that directly convert silicon tetrachloride into silane face many of the same corrosion and purification problems.

SUMMARY OF THE INVENTION

We have discovered that silane can be made by reacting certain organic silicon compounds with hydrogen. The organic silicon compound can be prepared by reacting a silicon tetrahalide with certain organic compounds, which produces the organic silicon compound and an hydrohalic acid, such as hydrochloric acid. The first step of the process, the production of the organic silicon compound and the hydrochloric acid, occurs at a low temperature and results in the vaporization of the hydrochloric acid and its separation from the product. Because of the low temperature there is less corrosion by the hydrochloric acid, and the removal of the hydrochloric acid results in a very pure silane product because corrosion products are minimized. The second high temperature reaction, which forms the silane, occurs without the production of any highly corrosive by-products, which means that lower cost equipment can be used and that the resulting silane product will be purer. In addition, the silane product can be easily separated at room temperature from the by-products of the reaction because their boiling points are quite different. The production of a high purity silane is also favored because any contaminants that might be present are likely to have a lower vapor pressure than the silane and will therefore remain with the by-products. The process of this invention uses inexpensive raw materials, such as silicon tetrachloride, and can easily accommodate intermediate purification steps to further increase the purity of the silane product.

DESCRIPTION OF THE PREFERRED EMBODIMENT

In the first step of the process of this invention, a silicon tetrahalide having the general formula $SiX_4$ is reacted with an organic compound to produce an organic silicon compound and hydrohalic acid according to the following equation:

$$SiX_4 + 4RH \rightarrow SiR_4 + 4HX$$

In the above equation, X is halide and each R is independently selected from alkoxy to $C_4$, alkyl to $C_4$, alkylene to $C_4$, and alkinyl to $C_4$. That is, the organic compound, RH, can be an alcohol, an alkane, an alkene, an alkine, or a mixture thereof. In the formula, X is preferably chlorine because silicon tetrachloride is inexpensive and readily available. The R group is preferably alkyl, and, of the alkyls, preferably methyl, as the resulting product, tetramethylsilicon, is more stable and methane is inexpensive. Another R group that has advantages is methoxy since methanol is inexpensive and readily available and silicon tetramethoxide is relatively stable. In this reaction, the reactants are preferably mixed in stoichiometric proportions, although 5% by weight less silicon tetrahalide than stoichiometric or 10% by weight more than stoichiometric of the organic compound could be used. It is, in fact, preferable to use about 10% by weight in excess of stoichiometric of the organic compound in order to help distill off any hydrohalic acid that is trapped in the alkylsilane. If the organic compound is a liquid, it is preferable to conduct the reaction at a temperature between room temperature and the boiling point of the organic compound, and preferably at the boiling point of the organic compound in order to more effectively separate the hydrohalic acid. If the organic compound is a gas, however, it is preferable to conduct the reaction at a temperature above the boiling point of the silicon tetrahalide to enhance contact between the two compounds. The reaction is over when the formation of hydrohalic acid ceases. At that time, the reaction mixture is cooled to room temperature. The resulting organic silicon compound is generally a liquid at room temperature.

It may be desirable to purify the organic silicon compound before proceeding to the next step in the process of this invention. Purification can be accomplished, for example, by heating the organic silicon compound and passing it through a column to strip the hydrohalic acid from it, a procedure well known in the art.

In the next step of the process of this invention, the organic silicon compound is reacted with hydrogen to form silane and an organic by-product according to the equation:

$$SiR_4 + 4H_2 \rightarrow SiH_4 + 4RH$$

In this reaction, the organic silicon compound and the hydrogen can be reacted stoichiometrically, although it is preferable to use excess hydrogen, up to 50 mole % in excess of stoichiometric, in order to insure a complete reaction. The excess hydrogen can be recovered and recycled. This reaction is preferably performed at a temperature above the boiling point of the organic silicon compound. The reaction time for a particular set of reactants conditions is determined experimentally by repeating the reaction for various periods of time, followed by cooling, collecting, and analyzing the reaction products. When the reaction is complete, the reaction mixture is cooled to liquify any unreacted organic silicon compound so that it can be removed. The reaction mixture is then further cooled, which liquifies the organic by-product which is also removed. Further cooling then liquifies the silane which is collected as the product. The silane can further be purified by a fractional distillation process well known in the commercial art. By processes well known in the art, the silane product can be decomposed by heating to form very pure silicon for use in making transistors and other electronic devices.

The following example further illustrates this invention.

EXAMPLE

A jacketed reaction vessel fitted with a pressure gauge is charged with 170 grams of silicon tetrachloride and 70 grams of methane. The reaction mixture is heated to a temperature of about 100° C. After the evolution of hydrochloric acid from the reaction mixture ceases, the reaction mixture is cooled and the product, tetramethylsilicon, is collected. The tetramethylsilicon is then distilled at a temperature of about 65° C. to strip off any hydrochloric acid that may be present. The purified tetramethylsilicon (about 88 grams) is placed in a second reaction vessel with 12 grams of hydrogen and heated to a temperature of 400° C. for one hour. Upon cooling to a temperature of about 65° C., unreacted tetramethylsilicon condenses and is removed. At a temperature of $-112°$ C., silane condenses and is collected. The methane is then separated from the excess hydrogen using gas permeators.

We claim:

1. A method of making silane comprising reacting a compound having the general formula $SiR_4$ with hydrogen, where each R is independently selected from the group consisting of alkoxy to $C_4$, alkyl to $C_4$, alkylene to $C_4$, and alkinyl to $C_4$.

2. A method according to claim 1 wherein each R is alkyl to $C_4$.

3. A method according to claim 1 wherein each R is methyl.

4. A method according to claim 1 wherein the amount of said hydrogen is stoichiometric up to about 50 mole % in excess of stoichiometric.

5. A method according to claim 1 including the additional last steps of cooling to condense silane and separating said condensed silane.

6. A method according to claim 5 including the additional last step of heating said silane to decompose it and deposit silicon.

7. A method according to claim 1 wherein said reaction is performed at a temperature above the boiling point of said $SiR_4$.

8. A method of making silane comprising:
   (1) reacting a silicon tetrahalide having the general formula $SiX_4$ with a compound selected from the group consisting of alcohols to $C_4$, alkanes to $C_4$, alkenes to $C_4$, alkines to $C_4$, and mixtures thereof, where each X is independently selected from halogens, to produce a product having the general formula $SiR_4$, where each R is independently selected from the group consisting of alkoxy to $C_4$, alkyl to $C_4$, alkylene to $C_4$, and alkinyl to $C_4$; and
   (2) reacting said $SiR_4$ with hydrogen to produce said silane.

9. A method according to claim 8 wherein each X is chlorine.

10. A method according to claim 8 wherein said compound is an alkane to $C_4$.

11. A method according to claim 10 wherein said alkane is methane.

12. A method according to claim 8 wherein step (1) is performed at a temperature between room temperature and the boiling point of said compound when said compound is a liquid, and at a temperature above the boiling point of said $SiX_4$ when said compound is a gas, and step (2) is performed at a temperature above the boiling point of said $SiR_4$.

13. A method according to claim 8 including the step between step (1) and step (2) of purifying said $SiR_4$ by heating said $SiR_4$ in a column to strip HX therefrom.

14. A method according to claim 8 wherein $SiX_4$ is $SiCl_4$, said compound is an alcohol to $C_4$, and $SiR_4$ is $Si(OCH_3)_4$.

15. A method according to claim 8 including the additional last step of heating said silane to produce silicon.

* * * * *